US008057393B2

(12) United States Patent
Yao et al.

(10) Patent No.: US 8,057,393 B2
(45) Date of Patent: Nov. 15, 2011

(54) METHOD AND DEVICE FOR TRANSMISSION OF A WIDE-BEAM IN AN ULTRASONIC DIAGNOSTIC SYSTEM

(75) Inventors: Bin Yao, Shenzhen (CN); Qinjun Hu, Shenzhen (CN); Bo Yang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1096 days.

(21) Appl. No.: 11/855,418

(22) Filed: Sep. 14, 2007

(65) Prior Publication Data

US 2008/0125660 A1 May 29, 2008

(30) Foreign Application Priority Data

Nov. 28, 2006 (CN) .......................... 2006 1 0157173

(51) Int. Cl.
*A61B 8/00* (2006.01)

(52) U.S. Cl. ....................................................... 600/443

(58) Field of Classification Search .................. 600/437, 600/439, 443, 447, 407
See application file for complete search history.

(56) References Cited

U.S. PATENT DOCUMENTS 5,951,479 A 9/1999 Holm et al.
6,193,659 B1 2/2001 Ramamurthy et al.
6,282,963 B1 9/2001 Haider
6,585,548 B2 7/2003 McCarthy
6,585,648 B1 7/2003 Robinson
7,785,260 B2 * 8/2010 Umemura et al. ............ 600/447
2002/0068869 A1 * 6/2002 Brisken et al. ................ 600/439
2003/0199763 A1 * 10/2003 Angelsen et al. ............. 600/437
2010/0217124 A1 * 8/2010 Cooley .......................... 600/443

OTHER PUBLICATIONS

Song Cunniu, et al., “Variable focal length of ultrasound focusing transducer,” Journal of Shaanxi Normal University (Natural Science Edition), vol. 25, No. 4, Dec. 1997.
Wang Bo et al., “Tolerance Analysis and Apodization Processing of Medical Ultrasound Array Transducer Wave Beams,” Journal of Xi’an Jiaotong University, vol. 33, No. 3, Mar. 1999.

* cited by examiner

*Primary Examiner* — Brian Casler
*Assistant Examiner* — Amanda Lauritzen
(74) *Attorney, Agent, or Firm* — Kory D. Christensen; Stoel Rives LLP

(57) ABSTRACT

A method and device for transmission of wide beam in ultrasonic diagnostic systems is disclosed. The method comprises: dividing an aperture of an ultrasonic probe into N sub-apertures; laterally dividing a focus into N sub-focuses, wherein the N sub-apertures correspond to the N sub-focuses respectively, each sub-aperture has M array elements which all focus on a sub-focus corresponding to said sub-aperture; and N and M are integers larger than 2; exciting the N sub-apertures by a pulse generator, so as to obtain a laterally stretched transmit acoustic filed, wherein the transmit acoustic fields of the N sub-apertures focus on the corresponding sub-focuses respectively; and accumulating the acoustic fields of the sub-apertures to form an acoustic field of a wide beam covering acoustic fields of all receive lines. The present invention makes it possible for the system to transmit wide beams covering all receive lines, by dividing the aperture of the probe into a plurality of sub-apertures and accumulating the acoustic fields of the sub-apertures.

10 Claims, 4 Drawing Sheets

1 2 3 4 1 2 3 4 1 2 3 4 1 2 3 4 direction of depth

| 1 | 2 | 3 | 4 | 1 | 2 | 3 | 4 | 1 | 2 | 3 | 4 | 1 | 2 | 3 | 4 |
|---|---|---|---|---|---|---|---|---|---|---|---|---|---|---|---|
| 1 | 1 | 1 | 1 | 2 | 2 | 2 | 2 | 3 | 3 | 3 | 3 | 4 | 4 | 4 | 4 |
| 1 | 2 | 1 | 2 | 1 | 2 | 1 | 2 | 3 | 4 | 3 | 4 | 3 | 4 | 3 | 4 |

METHOD AND DEVICE FOR TRANSMISSION OF A WIDE-BEAM IN AN ULTRASONIC DIAGNOSTIC SYSTEM

FIELD OF THE INVENTION

The present invention generally relates to imaging techniques for medical ultrasonic diagnostic systems, and in particular to a method and device for transmission of wide-beam in an ultrasonic diagnostic system.

BACKGROUND OF THE INVENTION

Fast imaging plays an important role in an ultrasonic diagnostic system in that it helps to provide a basis for more advanced techniques, i.e. a high data rate. With more information collected within a unit time, it becomes possible to perform finer image analysis and implement various techniques well. In particular, its advantages are as follows:

1. Improvement on 3D/4D Imaging

Both 3D and 4D imaging are on the basis of processing an extremely large amount of data. The imaging rate may be limited by the relatively low frame rate, which in turn poses limitations on 3D image speed.

2. Improvement on Blood Flow Imaging

The frame rate and image quality of blood flow imaging both have a direct influence on the interaction between a user and the system, which is an important criterion on the system level. In some systems, the frame rate of flow imaging is under that of C mode in some advanced systems. Thus the fast imaging is very important. To make it simple, the principle of fast imaging lies in generating the data of a plurality of scan-lines with the data received during one transmission, which helps to obtain the data of scan-lines in parallel. As a result, the frame rate of flow imaging can be increased significantly.

3. Improvement on Cardiac Imaging

For a heart moving fast, the frame rate is sometimes even more important than image quality.

4. Improvement on Image Quality

Many prior arts may be summed up as coming under different tradeoffs between image quality and frame rate, e.g.:

i) Synthesis aperture uses two transmissions to synthesize one scan-line with high signal to noise ratio.

ii) Composite imaging improves the image quality and reduces speckles by repeatedly transmitting composite scan-lines at different angles.

iii) It takes several transmissions to reduce the effect of longitudinal side lobes during the transmission of Golay code in coded excitation.

iv) In B mode imaging of heart, high frame rate is achieved by using low-density scan.

In the above-described examples, i)-iii) improve image quality at the expenses of frame rate, while iv) increases frame rate at the expenses of image quality. This contradiction between image quality and frame rate can be relieved by the fast imaging, which helps to implement these techniques in a better way.

5. Improvement on Heart-Related Techniques

In prior arts, many advanced systems are related to clinical techniques of heart, such as anatomic M-mode and the related analysis on the movement of heart. These techniques use the variation over time of the location of a certain part of heart in the image to conduct clinical evaluation and indicator calculation, in order to get a continuous image and a precise result. This imposes a critical requirement on the time resolution of the heart image, while the time resolution is actually the frame rate of image.

Multi-beam reception has become the focus of study for the purpose of improving frame rate. In multi-beam reception, a plurality of scan-lines is received during one transmission so as to reduce the time needed to generate one image frame, and thereby improve the frame rate significantly. A main problem associated with this technique is distortion, i.e., obtained scan-lines will be distorted if the transmit beam does not cover all the scan-lines. Therefore, an important issue concerned with multi-beam techniques is to make the transmit beam to cover a range of received scan-lines, i.e., a technique for transmission of wide beam.

A method of transmission of wide beam is disclosed in U.S. Pat. No. 6,585,648, titled "System, method and machine readable program for performing ultrasonic fat beam transmission and multilane receive imaging", wherein the transmit waveforms of a plurality of transmissions are accumulated to obtain a wide transmit beam. According to this patent, for a single beam, the transmission of each beam corresponds to different delayed transmit waveforms of a plurality of array elements; for various scan-lines, delays of transmit waveforms are different from each other. As a result, incorporating a plurality of transmission into one will accumulate a plurality of transmit waveforms of one array element and a composite waveform of the wide beam of the array element is obtained. Since the delays are different from each other, the transmit waveforms obtained at each array element are different from each other as well. The transmission result of such a waveform can be actually regarded as an accumulation of acoustic fields generated by single beam transmissions, thereby a wide beam is obtained.

A method for optimization of ultrasonic beam is disclosed in U.S. Pat. No. 6,282,963, titled "Numerical optimization of ultrasound beam path". The main principle of the patent is to obtain a wide beam by optimizing the transmit apodizing curves. This method mathematically models the transmit beam (taking into account the effect of the apodizing curves) and proposes criterions on evaluation of wide beam. An optimized transmit apodizing curve is obtained by optimizing math equations.

The above-discussed techniques have the disadvantages that wide beam is obtained by transmitting any waveform (U.S. Pat. No. 6,585,648) or by controlling the transmit apodizing curve (U.S. Pat. No. 6,282,963). However, the premise for implementing these methods is that a front end of an ultrasonic system can transmit arbitrary waveform, which is impossible for lots of ultrasonic systems that can transmit only excitation waveform of unipolar or bipolar levels.

SUMMARY OF THE INVENTION

The object of the present invention is to propose a method and device for implementing transmission of wide beam in unipolar or bipolar ultrasonic systems, so as to address the above-discussed disadvantages of the prior arts.

In one aspect of the present invention, a method for transmission of a wide beam in an ultrasonic diagnostic system is provided, the method comprises steps of:

dividing an aperture of an ultrasonic probe into N sub-apertures;

laterally dividing a focus into N sub-focuses, wherein the N sub-apertures correspond to the N sub-focuses respectively, each sub-aperture has M array elements; and N and M are integers larger than 2;

exciting the N sub-apertures by a pulse generator, so as to obtain a laterally stretched transmit acoustic filed, wherein the transmit acoustic fields of the N sub-apertures focus on the corresponding sub-focuses respectively; and the acoustic fields of the sub-apertures are accumulated to form an acoustic field of a wide beam covering acoustic fields of all receive lines.

Preferably, the transmit aperture is equidistantly divided into N sub-apertures and the focus is laterally divided into N sub-focuses equally spaced.

Preferably, the array elements of the N sub-apertures are arranged in the order of arranging the N sub-apertures.

Preferably, the N*M array elements of the N sub-apertures are alternately arranged.

In another aspect of the present invention, a device for transmission of wide beam in an ultrasonic diagnostic system is provided, the device comprises:

a probe, a transmitting/receiving converter, and a pulse generator; wherein the pulse generator converts a digital signal into an analog signal according to transmit waveform and transmit delay, so as to excite array elements of the probe; the array elements of the probe are excited to transmit ultrasonic waves which penetrates body tissues and produces echoes; and the probe enters a receiving mode after the transmission;

wherein the transmit aperture of the probe is divided into N sub-apertures; a focus of the probe is laterally divided into N sub-focuses; the N sub-apertures correspond to the N sub-focuses respectively; each of the sub-apertures has M array elements; the pulse generator excites the N sub-apertures to obtain a laterally stretched transmit acoustic field, the acoustic fields of the N sub-apertures focus on the corresponding sub-focuses respectively; and the acoustic fields of the sub-apertures are accumulated to form a acoustic field of a wide beam covering the acoustic fields of all receive lines; and the N and M are integers larger than 2.

The device for transmission of wide beam in ultrasonic diagnostic systems of the present invention has the advantages over the prior arts that it makes it possible for an ultrasonic system transmitting unipolar or bipolar transmit waveform to transmit a wide beam covering all receive lines, by dividing the aperture of the probe into a plurality sub-apertures and accumulation of the acoustic fields of the sub-apertures after focusing.

DETAILED DESCRIPTION OF THE PREFERRED EMBODIMENT

The device and method of the present invention are now discussed in detail with reference to the following embodiments and the drawings.

Figure 1:
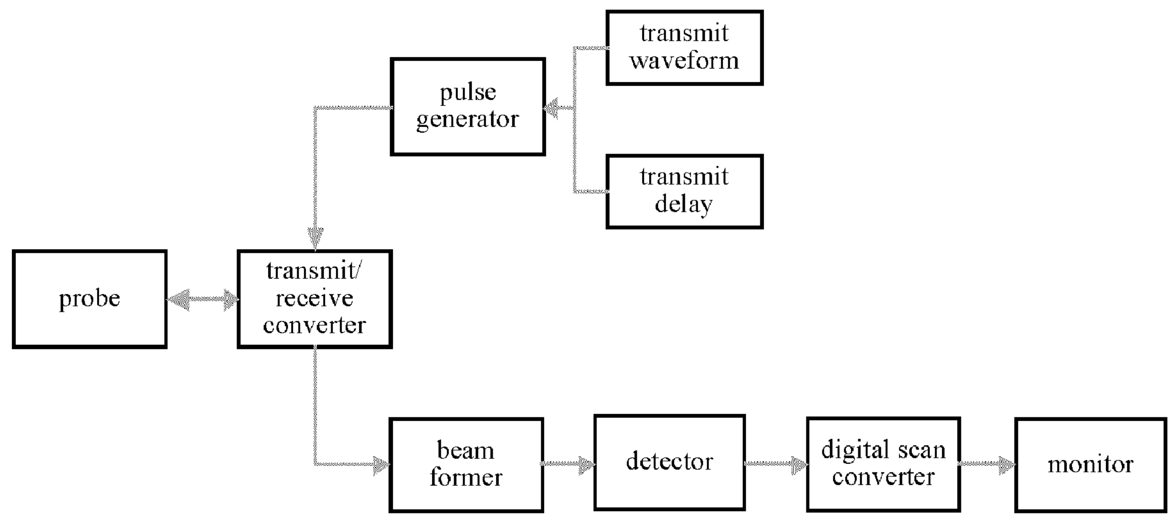
FIG. 1 shows a block diagram of an ultrasonic imaging system according to an embodiment of the present invention.

FIG. 1 shows a block diagram of a medical ultrasonic imaging system according to an embodiment of the present invention. For each channel of an ultrasonic probe, a transmit waveform and a transmit delay are set during transmission. A pulse generator converts a digital signal of the transmit waveform to an analog signal so as to excites the array elements of the probe. The array elements are excited to generate ultrasonic waves which penetrate body tissues and produces echoes. The probe enters a receiving mode after transmission. The echoes data of a plurality of channels are passed a beam former to form scan-line data. The current scan-line data is still a high frequency data which needs to be demodulated and processed by a detector. Then the data processed by a digital scan converter can be displayed on a monitor.

Figure 2:
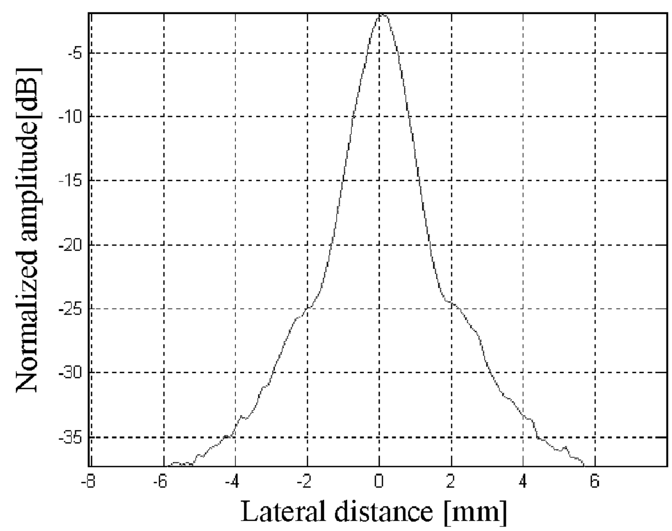
FIG. 2 schematically illustrates the cross section of an acoustic field strong focusing at the focus in the case of a single beam.

In the case of conventional transmission of a single beam, for the purpose of improving lateral resolution of an image, it is desired that the energy of an ultrasonic beam is collected as laterally as possible, i.e., the beam is as thin as possible. Accordingly, strong focusing is used such that the energy of the acoustic field is collected on the receive lines. For a given transmit aperture, a time delay is calculated by determining the time needed for the beam to travel from each array element to a focus. A bundle of focused beams is formed by exciting the array elements at different times. FIG. 2 shows the cross section of the acoustic field at the focus in the case of a single beam. The position of the receive line is at a zero point of the lateral distance, and the maximum energy is collected at this point. Therefore, the receive line has a good lateral resolution.

In order to receive a plurality of beams, it is desired that the energy of the acoustic field is focused in one area that covers a range of all receive lines and the energy of the acoustic field in this range is flat. An ideal acoustic field is box-like, i.e., the energy is equally spread within the range of receiving beams and little energy is outside this range. The embodiment of the present invention provides a method and device for transmission of a wide beam. According to the embodiment, a transmit aperture is divided into a plurality of sub-apertures, and each of the sub-apertures focuses on a different point in the acoustic field. By means of such a transmission method, the acoustic fields of these sub-apertures are mutually accumulated, so as to form a acoustic field of an uniform wide beam.

In one embodiment, an aperture of an ultrasonic probe is divided into N sub-apertures and a focus is laterally divided into N sub-focuses; the N sub-apertures correspond to N sub-focuses respectively, and each sub-aperture has M array elements which all focus on a sub-focus corresponding to the sub-aperture; wherein N and M may be any integers larger than 2. A pulse generator excites the N sub-apertures to obtain a laterally stretched transmit acoustic field, the acoustic fields of the N sub-apertures focuses on the corresponding sub-focus respectively; the acoustic fields of all the sub-apertures are accumulated to form a acoustic field of a wide beam covering all receive lines. Therefore, there are various ways for grouping the sub-apertures into different groups, and the amount of the groups may be different.

Figures 3, 4:
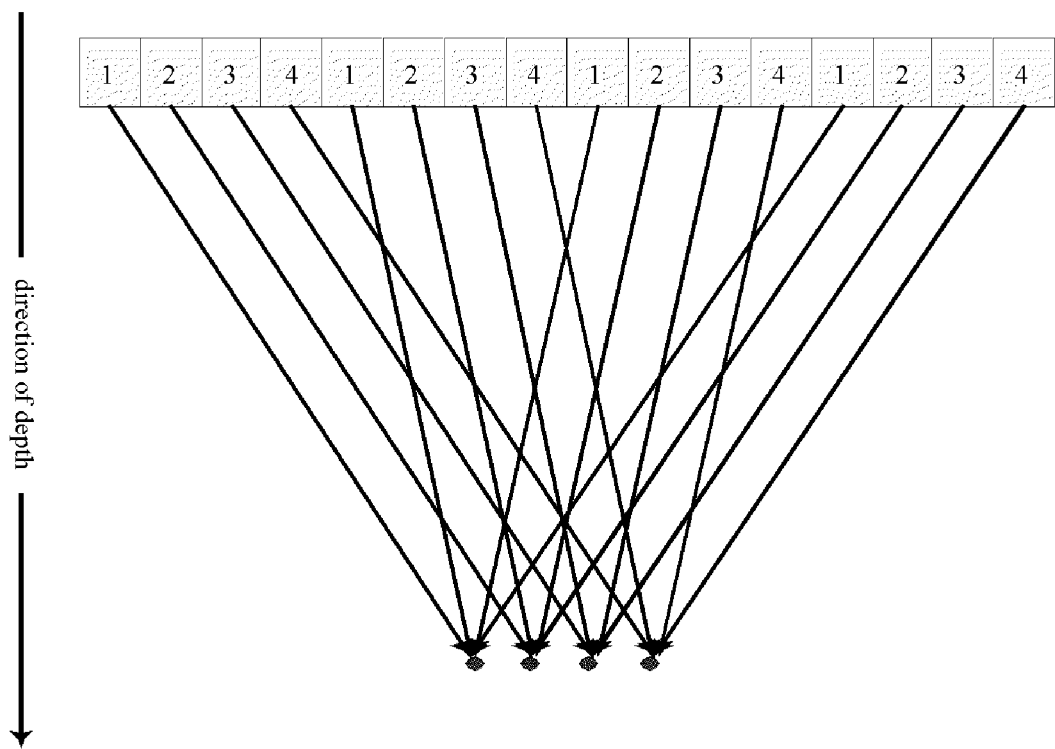
FIG. 3 shows an exemplary method for grouping sub-apertures of a transmit aperture according to an embodiment of the present invention.
FIG. 4 schematically illustrates the manner of focusing transmissions of the sub-apertures according to an embodiment of the present invention.

FIG. 3 illustrates three ways of dividing a transmit aperture with 16 array elements into four sub-apertures. As shown in FIG. 3, the second row shows that the array elements of the four sub-apertures are arranged in the order of arranging the sub-apertures, while the first and third rows show that the four sub-apertures are alternately arranged according to a certain rule. The methods for grouping the sub-apertures conform to a confined rule that steering angles of the array elements, a pitch of the array elements as well as the location of focusing area are appropriately set; after dividing the transmit aperture to form the sub-apertures, the pitch of the array elements of the sub-aperture may increase; if the pitch of the array elements is too long, sizes of side lobes and grating lobes will increase; the pitch of the array elements of a sub-aperture should be sufficient small if the steering angle is small; otherwise the acoustic fields of the sub-apertures may not focus well enough or even can not focus at all; if, with different depths of the focusing area, the possible number of groups should be limited, the smaller the depth of focusing area is, the smaller a number of groups of the sub-apertures is. Therefore, the amount of groups and the grouping method can both be optimized based on these parameters.

The same number of sub-focuses as that of sub-apertures are equidistantly arranged on both side of the centre of the transmit aperture, with respect to the position of focus depth, each sub-focus corresponds to one sub-aperture and the transmission of the sub-aperture focuses on the sub-focus, as shown in FIG. 4. Assuming that FLen is a width of the focusing area, if a number of receive scan-lines in each transmission is RLnum and the distance between the scan-lines is RLdist, the width D of the transmit acoustic field should be larger than the range covering receive lines, i.e., $$FLen=(RLnum-1)*RLdist \tag{1}$$

Figure 5:
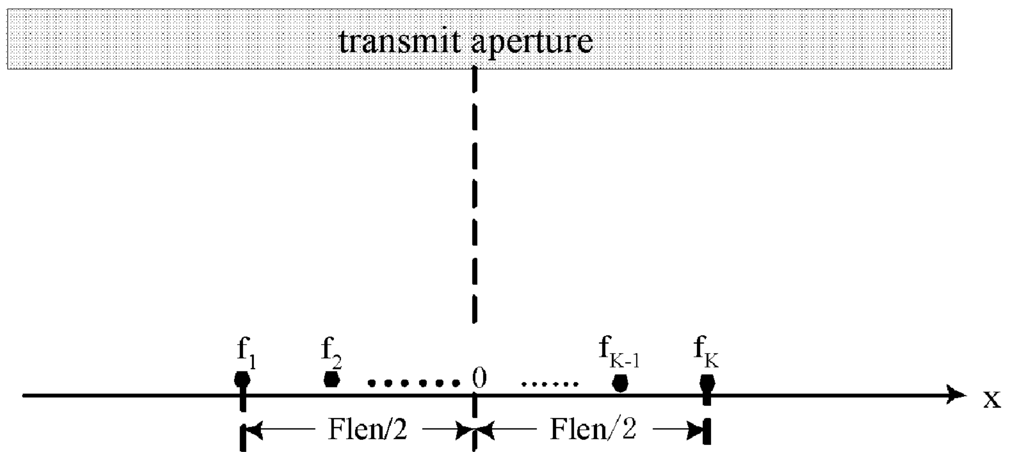
FIG. 5 schematically illustrates an arrangement of sub-focuses according to an embodiment of the present invention.

Assuming that the transmit aperture is divided into K groups. A method for grouping the sub-focuses is shown in FIG. 5. A focusing area is a central area of the transmit aperture and covers a range of receive scan-lines. As shown in FIG. 5, $f_1$ and $f_x$ are arranged on both side of the focusing area and other points are distributed therein evenly. That is:

$$f_1=-FLen/2$$

$$f_K=FLen/2$$

$$f_i=(i-1)\cdot(f_K f_1)/(K-1)+f_1 \tag{2}$$

If {x} (i=1, . . . , N) are the N array elements of the transmit aperture, the transmit aperture is divided into K sub-apertures, and $\{F_k\}$ (k=1, . . . , K) are the sub-focuses, then the delay for each array element can be written as:

$$G(x_i)=\{F_k|\text{the sub-focus corresponding to the sub-aperture containing } x_i\}$$

$$T_{dist}(i)=d(x_i, G(x_i))/v_{sound}$$

$$T_{delay}(i)=\max(T_{dist}(i))-T_{dist}(i) \tag{3}$$

where $G(x_i)$ is the sub-focus corresponding to $x_i$, $v_{sound}$ is the velocity of ultrasonic, $T_{dist}$ is the time needed for the ultrasonic to travel from the array element to the corresponding sub-focus, $T_{delay}$ is the transmit delay of the array element.

Figure 6:
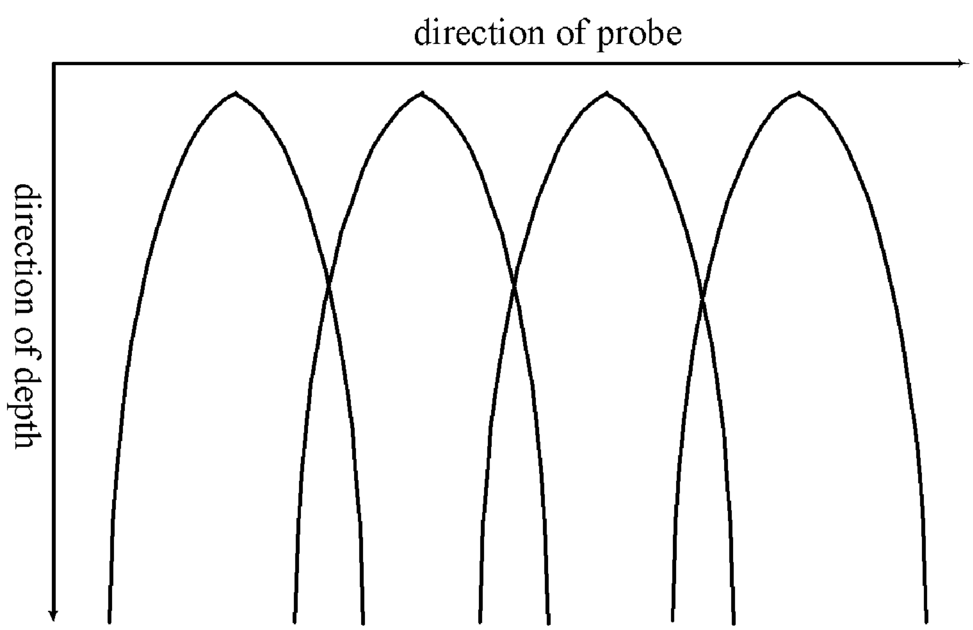
FIG. 6 shows a cross section of an acoustic field with four sub-focuses.
Figure 7:
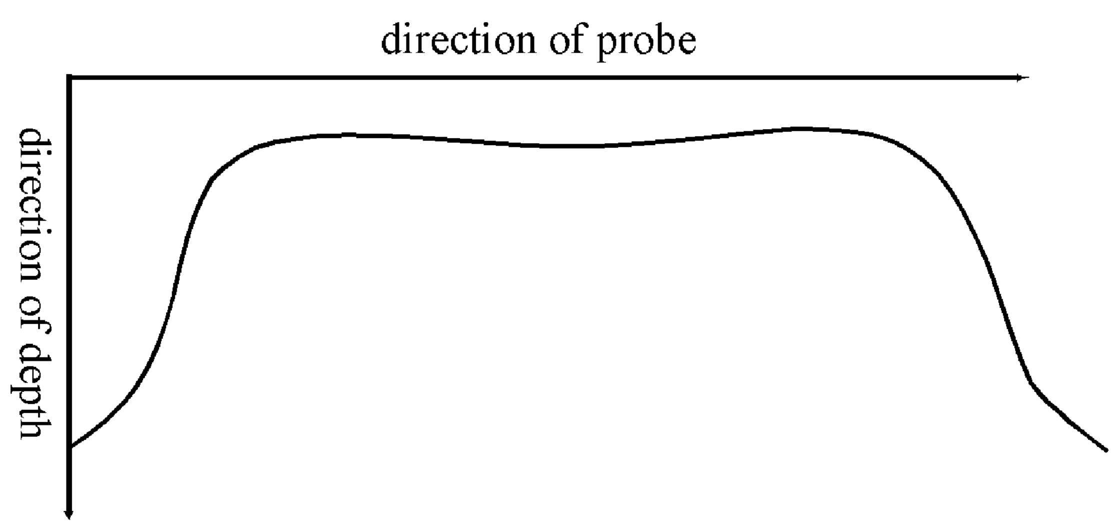
FIG. 7 schematically illustrates formation of a wide beam in the case of four sub-focuses of FIG. 6.

After each array element performs the transmission according to its delay, the resultant acoustic field is dividable. As shown in FIG. 6, each sub-aperture has its respective sub-focus. At the depth of each sub-focus, a beam is formed by focusing the transmit beam of the sub-aperture at the sub-focus. FIG. 6 shows an acoustic field with four sub-focuses. The acoustic fields of the four sub-apertures are accumulated to obtain an acoustic field of wide beam, as shown in FIG. 7. According to this design, the wide beam covers a range of all receive lines. Therefore, the echoes of this range include the information on all the receive lines. The echo data for each receive line can be obtained by use of a parallel beam synthesis method.

The invention claimed is:

1. A method for transmission of a wide beam in an ultrasonic diagnostic system, comprising steps of:

dividing a transmit aperture of an ultrasonic probe into N sub-apertures;

laterally dividing a focus of a desired transmit acoustic field into N sub-focuses, wherein the N sub-apertures correspond to the N sub-focuses respectively, each sub-aperture has M array elements, and N and M are integers larger than 2; and exciting the N sub-apertures by a pulse generator, so as to obtain a laterally stretched transmit acoustic field, wherein the transmit acoustic fields of the N sub-apertures focus on the corresponding N sub-focuses respectively, such that each element of a sub-aperture converges at a common focal point for that particular sub-aperture, and the transmit acoustic fields of the N sub-apertures are accumulated to form the laterally stretched transmit acoustic field of a wide transmit beam covering acoustic fields of a range of all receive lines obtained by parallel beam synthesis.

2. The method of claim 1, wherein the transmit aperture is equidistantly divided into N sub-apertures and the focus is laterally divided into N sub-focuses equally spaced.

3. The method of claim 1, wherein the array elements of the N sub-apertures are arranged in the order of arranging the N sub-apertures.

4. The method of claim 2, wherein the array elements of the N sub-apertures are arranged in the order of arranging the N sub-apertures.

5. The method of claim 1, wherein the N*M array elements of the N sub-apertures are alternately arranged.

6. The method of claim 2, wherein the N*M array elements of the N sub-apertures are alternately arranged.

7. A device for transmission of a wide beam in an ultrasonic diagnostic system, comprising:

a probe having a transmit aperture;

a transmitting/receiving converter;

a pulse generator, configured to convert a digital signal into an analog signal according to transmit waveform and transmit delay times and to excite array elements of the probe to transmit ultrasonic waves which penetrate body tissues and produce echoes, wherein the probe is configured to enter a receive mode after the transmission;

wherein the transmit aperture of the probe is divided into N sub-apertures; wherein the probe is configured to laterally divide a focus of a desired transmit acoustic field into N sub-focuses;

wherein the N sub-apertures correspond to the N sub-focuses respectively, and each of the sub-apertures has M array elements;

wherein the pulse generator is configured to excite the N sub-apertures to obtain a laterally stretched transmit acoustic field, and configured such that the acoustic fields of the N sub-apertures focus on the corresponding N sub-focuses, respectively, such that each element of a sub-aperture converges at a common focal point for that particular sub-aperture, and the probe is configured such that the transmit acoustic fields of the N sub-apertures are accumulated to form the laterally stretched transmit acoustic field of a wide transmit beam to cover the acoustic fields of a range of all receive lines obtained by parallel beam synthesis; and wherein the N and M are integers larger than 2.

8. The device of claim 7, wherein the N sub-apertures and the N sub-focuses are equidistantly arranged, respectively.

9. The device of claim 7, wherein the array elements of the N sub-apertures are arranged in the order of arranging the N sub-apertures.

10. The device of claim 7, wherein the N*M array elements of the N sub-apertures are alternately arranged.

* * * * *